United States Patent
Roa-Espinosa

(10) Patent No.: US 9,371,356 B2
(45) Date of Patent: Jun. 21, 2016

(54) SEPARATION OF BIOCOMPONENTS FROM MANURE

(71) Applicant: Aicardo Roa-Espinosa, Madison, WI (US)

(72) Inventor: Aicardo Roa-Espinosa, Madison, WI (US)

(*) Notice: Subject to any disclaimer, the term of this patent is extended or adjusted under 35 U.S.C. 154(b) by 446 days.

(21) Appl. No.: 13/929,618

(22) Filed: Jun. 27, 2013

(65) Prior Publication Data

US 2015/0005482 A1    Jan. 1, 2015

(51) Int. Cl.
| | |
|---|---|
| C02F 1/24 | (2006.01) |
| C02F 1/56 | (2006.01) |
| C02F 11/12 | (2006.01) |
| C02F 11/14 | (2006.01) |
| C02F 11/16 | (2006.01) |
| C05F 3/06 | (2006.01) |
| B03D 3/06 | (2006.01) |
| C07K 1/32 | (2006.01) |
| C02F 103/20 | (2006.01) |

(52) U.S. Cl.
CPC ... *C07K 1/32* (2013.01); *B03D 3/06* (2013.01); *C02F 1/24* (2013.01); *C02F 1/56* (2013.01); *C02F 11/121* (2013.01); *C02F 11/14* (2013.01); *C02F 11/16* (2013.01); *C02F 2103/20* (2013.01); *C02F 2303/24* (2013.01)

(58) Field of Classification Search
CPC ............... C02F 1/24; C02F 1/56; C02F 9/00; C02F 11/02; C02F 11/12; C02F 11/121; C02F 11/122; C02F 2103/20; C02F 2303/24; C02F 11/14; C02F 11/16; C05F 3/00; C05F 3/06; C05F 9/04; C05F 1/00; C05F 1/02; C05F 1/007; B03D 1/02; B03D 1/06; B03D 1/08; B03D 1/082; B03D 1/085; B03D 3/00; B03D 3/02; B03D 3/06; B03D 2203/001; B03B 5/28; B03B 5/44

USPC ......... 71/15, 21; 209/162–167; 210/631, 632, 210/703–705, 732–736, 770, 800, 804
See application file for complete search history.

(56) References Cited

U.S. PATENT DOCUMENTS

| | | | | |
|---|---|---|---|---|
| 1,547,732 | A * | 7/1925 | Broadbridge | C05B 11/02 209/166 |
| 4,338,337 | A | 7/1982 | Frankl | |
| 4,526,791 | A | 7/1985 | Young | |
| 4,981,582 | A * | 1/1991 | Yoon | B01F 5/0408 209/164 |
| 5,161,694 | A * | 11/1992 | Yoon | B03B 1/04 209/165 |
| 5,316,682 | A * | 5/1994 | Keyser | B01F 5/0476 210/195.2 |
| 6,409,788 | B1 * | 6/2002 | Sower | A23K 1/106 71/11 |
| 6,413,433 | B1 * | 7/2002 | Maury | C02F 11/14 210/714 |
| 6,524,632 | B2 | 2/2003 | Kartchner | |
| 8,691,551 | B1 * | 4/2014 | Lahtinen | C12P 3/00 435/243 |

(Continued)

*Primary Examiner* — Joseph Drodge
(74) *Attorney, Agent, or Firm* — Steven H. Greenfield; Greenfield Invention and Patent Consulting, Inc.

(57) ABSTRACT

A process for separating amino acids and peptides from raw and digested farm manure is disclosed. The raw manure may be recovered from sand bedding used in the cow stalls of some farms. The process involves the steps of precipitating out struvite and separating a stream rich in amino acids and peptides from a mineral rich stream in a dissolved air floatation machine. Struvite precipitation is accomplished by the addition of polydicyandiamide and an acrylate based polymer, while the separation of the stream rich in fibers, amino acids and peptides from a mineral rich streams is accomplished by the addition of an acrylamide chloride copolymer.

8 Claims, 3 Drawing Sheets

(56) References Cited

U.S. PATENT DOCUMENTS

| | | | | |
|---|---|---|---|---|
| 2005/0145566 A1* | 7/2005 | Haase | | C02F 11/04 210/620 |
| 2006/0228231 A1* | 10/2006 | Winzeler | | B09B 3/00 417/313 |
| 2006/0270801 A1* | 11/2006 | Hagiopol | | C08L 33/26 525/218 |
| 2006/0283806 A1* | 12/2006 | Kojima | | C02F 1/5245 210/725 |
| 2009/0193863 A1 | 8/2009 | Hunt et al. | | |
| 2009/0206028 A1* | 8/2009 | Jiang | | B01D 53/1468 210/603 |
| 2009/0301972 A1* | 12/2009 | Hines | | B03D 1/01 210/705 |
| 2011/0021670 A1* | 1/2011 | Roa-Espinosa | | C02F 1/5236 524/17 |
| 2011/0021807 A1* | 1/2011 | Roa-Espinosa | | C07C 67/03 560/129 |
| 2011/0131873 A1* | 6/2011 | Soane | | C02F 1/40 44/608 |
| 2011/0252701 A1* | 10/2011 | Soane | | C10L 5/00 44/621 |
| 2013/0292329 A1* | 11/2013 | Northrop | | B09C 1/10 210/602 |
| 2014/0346108 A1* | 11/2014 | Josse | | C02F 1/20 210/605 |

* cited by examiner

SEPARATION OF BIOCOMPONENTS FROM MANURE

FIELD OF THE INVENTION

The present invention relates generally to a process of recovering useful materials from waste streams such as farm manure. More specifically, the process of the present invention is configured to separate a stream rich in large fibers, small fibers, amino acids and peptides from a mineral rich stream from raw and digested farm manure for use in fertilizers and beneficial microorganism growth.

BACKGROUND OF THE INVENTION

Waste streams such as farm manure contain components that are useful in many applications. These components include proteins that may be useful as feed, minerals that may be used as fertilizers and fibers that are useful as feedstock for biofuel production and mulches for lawn and garden. Manure is currently accumulated in ponds then pumped into large digesters where it undergoes anaerobic digestion. Alternatively, the raw manure is treated in outside lagoons.

A number of prior art references relate to the recovery of protein form waste streams. U.S. Pat. No. 4,526,791 discloses a fermentation process for converting agricultural waste material, including animal manure and crop wastes, into proteinaceous animal feed products. U.S. Pat. No. 4,338,337 teaches a method for recovering and recycling animal waste materials wherein the liquids and finer solid particles are converted into a high quality single cell protein by means of aerobic digestion. U.S. Pat. No. 6,524,632 describes a process for recovering the protein values from animal manure for reuse as animal feed. The process involves the use of an anaerobic digester to provide methane gas for combustion and use for heating and powering the facility including a radio wave generator for sterilizing the protein and solids being recovered for the feed. US publication number 20090193863 relates to a process for extraction and recovery of phosphorus from solid animal wastes comprising the steps of phosphorus extraction, phosphorus recovery, and phosphorus recovery enhancement. The process can be performed in batch or continuous mode.

SUMMARY OF THE PRESENT INVENTION

In one aspect of the present invention, a substantially continuous process for separating a stream rich in fibers, amino acids and peptides and a stream rich in minerals from raw farm manure, the process comprises the steps of: providing a raw manure stream for treatment, the manure stream containing amino acids, peptides fibers and minerals, the minerals containing nitrogen, phosphorus, potassium and sulfur; mechanically removing particles having a predetermined size; precipitating magnesium ammonium phosphate and calcium phosphate, the precipitating being accomplished by the addition of: between about 5 parts per million and about 75 parts per million on a dry weight basis of polydicyandiamide polymer, the polydicyandiamide polymer having a weight average molecular weight of between about 3000 and about 150,000; and separating a stream rich in amino acids, peptides and fibers from a stream rich in minerals, the separating being accomplished in a dissolved air flotation device by the addition of between about 10 parts per million and about 75 parts per million on a dry weight basis of acrylamide/Ethanaminium, N,N,N-trimethyl-2-((1-oxo-2-propenyl)oxo)-, chloride copolymer, the acrylamide/Ethanaminium, N,N,N-trimethyl-2-((1-oxo-2-propenyl)oxo)-, chloride copolymer having a weight average molecular weight of between about 3 million and about 10 million.

In another aspect of the present invention, a substantially continuous process for producing a stream rich in amino acids and peptides from digested farm manure comprises the steps of: providing a digested manure stream for treatment, the manure stream containing amino acids, peptides, fibers and minerals, the minerals containing nitrogen, phosphorus, potassium and sulfur; precipitating magnesium ammonium phosphate and calcium phosphate, the precipitating being accomplished by the addition of a polydicyandiamide the polydicyandiamide polymer being added at between about 5 parts per million and about 75 parts per million on a dry weight basis of polydicyandiamide polymer, the polydicyandiamide polymer having a weight average molecular weight of between about 3000 and about 150,000; passing the digested manure stream through a rotating drum and a screw press for mechanically removing particles having a predetermined size; and separating a stream rich in amino acids, peptides and fibers, the separating being accomplished by adding micronized air at a rate between 5 to 10 cubic feet per hour to the dissolved air flotation device by the addition of between about 10 parts per million and about 75 parts per million on a dry weight basis of acrylamide/Ethanaminium, N,N,N-trimethyl-2-((1-oxo-2-propenyl)oxo)-, chloride copolymer, the acrylamide/Ethanaminium, N,N,N-trimethyl-2-((1-oxo-2-propenyl)oxo)-, chloride copolymer having a weight average molecular weight of between about 3 million and about 10 million.

In yet another aspect of the present invention, a substantially continuous process for separating a stream rich in fibers, amino acids and peptides and a stream rich in minerals from raw farm manure, the process comprises the steps of: providing sand bedding material substantially saturated with raw manure; flushing the sand bedding with rinse water to remove the raw manure from the sand bedding to produce a flushed raw manure stream; the flushed raw manure stream containing magnesium ammonium phosphate, calcium phosphate, amino acids, peptides fibers and minerals, the minerals containing nitrogen, phosphorus, potassium and sulfur; mechanically removing particles having a predetermined size; precipitating magnesium ammonium phosphate and calcium phosphate, the precipitating being accomplished by the addition of between about 5 parts per million and about 75 parts per million on a dry weight basis of polydicyandiamide polymer, the polydicyandiamide polymer having a weight average molecular weight of between about 3000 and about 150,000; and separating the stream rich in amino acids, peptides and fibers from the stream rich in minerals, the separating being accomplished in a dissolved air flotation device by the addition of between about 10 parts per million and about 75 parts per million on a dry weight basis of acrylamide/Ethanaminium, N,N,N-trimethyl-2-((1-oxo-2-propenyl)oxo)-, chloride copolymer, the acrylamide/Ethanaminium, N,N,N-trimethyl-2-((1-oxo-2-propenyl)oxo)-, chloride copolymer having a weight average molecular weight of between about 3 million and about 10 million.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention.

A common process for treating raw farm manure is anaerobic digestion that may take place in tanks or lagoons. The benefits of anaerobic digestion include odor control, the potential for the production of methane that may be used as energy source and pathogen destruction. However, the amino acids, peptides, fibers and minerals that are contained in the manure are not separately recovered in the digestion process in a readily useable form.

It would therefore be desirable to provide a cost effective process for treating manure that provides for the separate recovery of the amino acids, peptides and fibers in one stream and the minerals in another stream. Amino acids and peptides may be beneficially used as animal feed, for biofuel production, microbe growth medium, adhesive manufacturing, biofertilizers and as reducing agents for nano materials. The fibers may be used as a source for biofuels, bio-fertilizers, mulch and bedding materials. Furthermore, it would be desirable to reduce the level of pathogens present in the manure that may be a source of diseases if humans come in contact with it.

While the process of the present invention may be beneficially used to separate raw manure, many farms are currently processing the raw manure in digesters or lagoons. An embodiment of the present invention process may be used for separating digested manure as well. Digesting manure produce methane gas useful for energy production as well as various nutrients and fibers useful in various agricultural applications. Farm manure may vary in consistency, but it most typically ranges from about 1% to about 10%.

Figure 1:
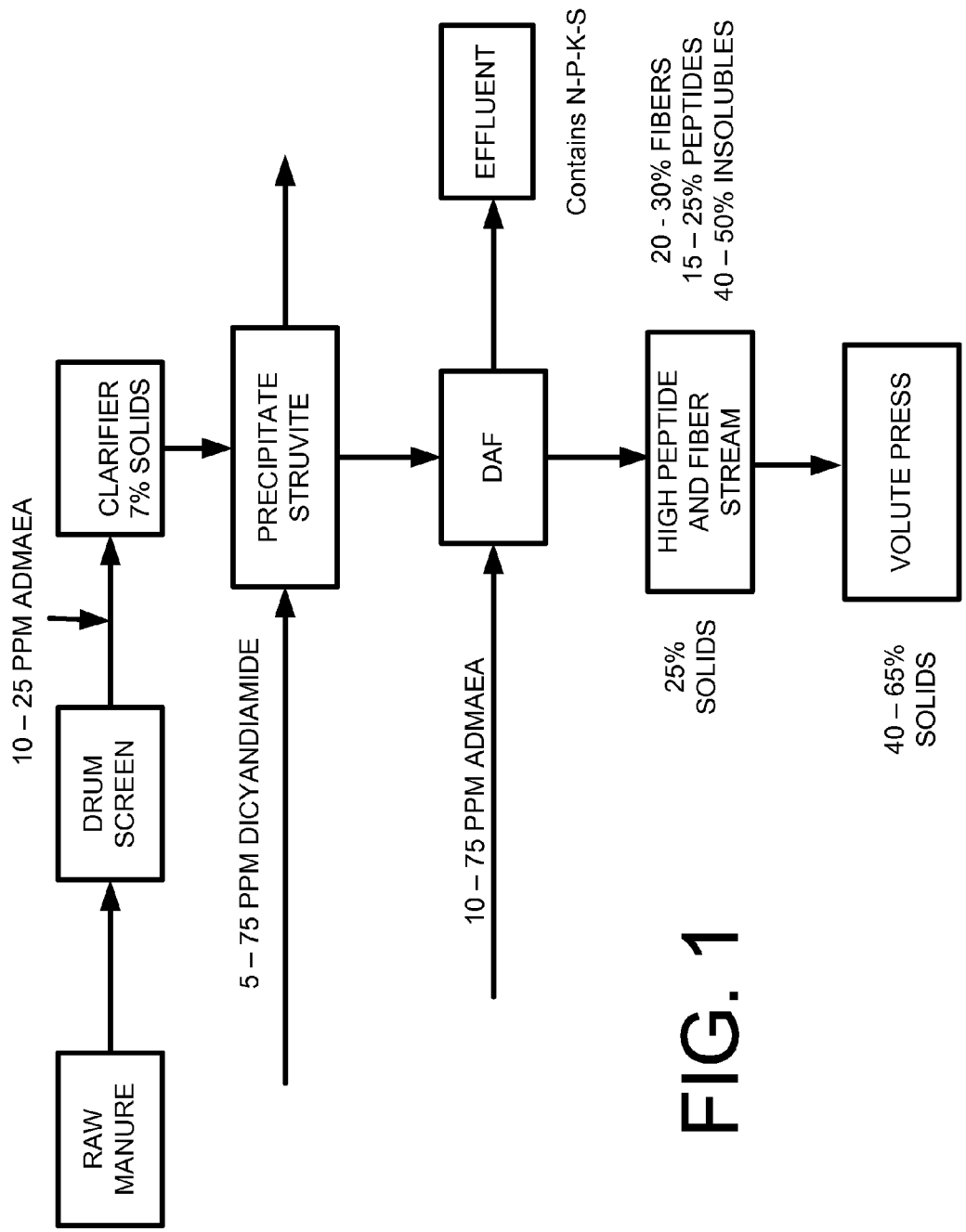
FIG. 1 is a flow chart of the process to recover amino acids, peptides and fibers from raw farm manure.

FIG. 1 is a depiction of the process for recovering amino acids, peptides and fibers from raw manure. In the first step, the manure undergoes a mechanical treatment to remove relatively large objects. This may be accomplished by a drum screen and a clarifier. Typical drum screen slot openings for this purpose range between about 10 mesh to about a 32 mesh. In the subsequent step, a polymer is added to precipitate magnesium ammonium phosphate, also referred to as struvite having the chemical formula of $NH_4MgPO_4.6H_2O$, and calcium phosphate. The polymer added is polydicyandiamide at a rate of between about 5 ppm to about 75 ppm on a dry weight basis.

In the next step, the stream is passed through a Dissolved Air Floatation (DAF) machine. DAF machines are configured to produce a high solids stream, typically at consistencies of about 25% and a low solids effluent stream of 1% solids or less using very small air bubbles injected into the incoming flow stream. The preferred air bubbles consist of micronized air of a size between about 10 micrometers and about 20 micrometers. The DAF machine separates the incoming stream into a stream having a relatively high solids and rich in amino acids, peptides and fibers and a low consistency effluent stream rich in mineral components which are mainly nitrogen (N), phosphorus (P), potassium (K) and sulfur (S).

In the process of the present invention, acrylamide/Ethanaminium, N,N,N-trimethyl-1-((1-oxo-2-propenyl)oxo)-, chloride copolymer (ADMAEA) is added at a rate of between 5 ppm to about 75 ppm on a dry basis to the DAF machine. The polymer helps insure that the high solids stream contains mostly amino acids, peptides and fibers, while the effluent stream contains mostly mineral components. These components include the elements of: nitrogen (N), phosphorus (P), potassium (K) and sulfur (S). In the present process, over 50% of the original nitrogen content, over 85% of the original sulfur content, about 20% of the original potassium content and over 85% of the original phosphorus content may be found in the effluent stream. The effluent may be further processed to recover specific mineral components or disposed of. This process embodiment may optionally also include the addition of 10-25 ppm of ADMAEA in the clarifier.

The stream having a relatively high content of amino acids, peptides and fibers coming out of the DAF machine has percent solids in the range of 20-30%. The percent solids of this stream may be further increased by processing it through a volute press presently used commercially such as a press made by Amcon®.

The fibers contained in the stream having a relatively high content of amino acids, peptides and fibers includes soluble fibers and fiber fragments having a distribution of between about 10 microns and 100 microns.

Raw manure has very high e-coli and coliform pathogen counts in the range of about $7\times10^5$ MPN/mL. The pathogen count is reduced after the clarifier before entering the DAF machine but it is still high as shown in Table 1. The pathogen count is significantly reduced to the range of about 200-500 by a combination of intense centrifuging and 50 ppm of ADMAEA. The DAF machine provides a centrifuging effect, but intense centrifuging may not be economical. Still, the low pathogen counts may be achieved by increasing the polymer dosage and optimizing other process variables.

Figure 2:
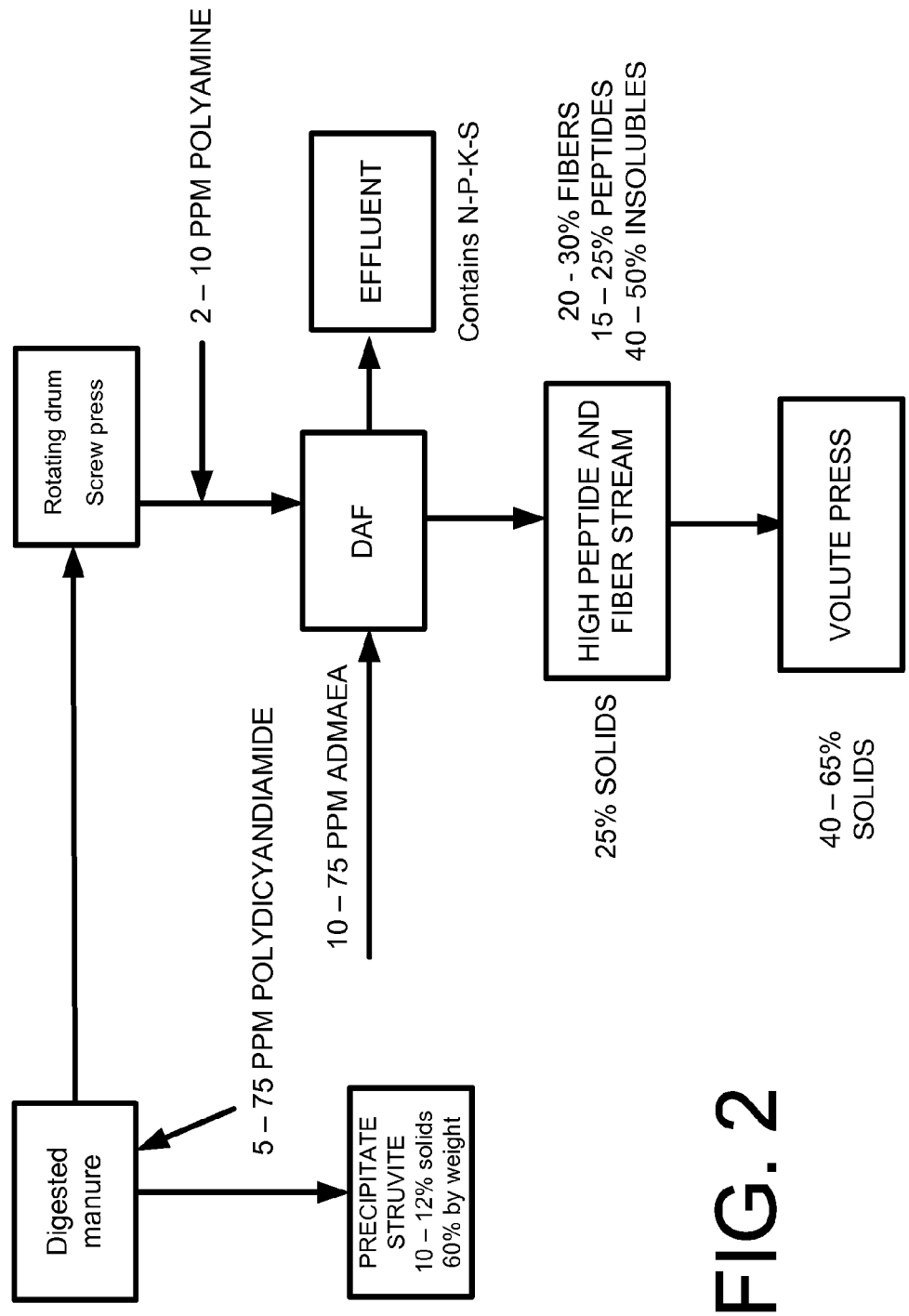
FIG. 2 is a flow chart of the process to recover amino acids, peptides and fibers from digested farm manure.

Another embodiment of the present invention process relates to treating a manure stream that has undergone digesting such as anaerobic digestion. A schematic for this embodiment is presented in FIG. 2. For this embodiment, struvite precipitation is the first step, followed by passage through a rotating drum and screw press where the stream is thickened to about 10-15% solids. A polyamine is then added at about 2-10 ppm after which the stream is treated in the DAF machine with ADMAEA. Most cationic polyamines are suitable for this application. The solids portion of the stream rich in amino acids, peptides and fibers may contain from about 15% to about 25% amino acids and peptides on a dry weight basis, which are the building block constituents of proteins, from about 25% to about 35% fibers and insoluble matter such as sand and calcium.

Figure 3:
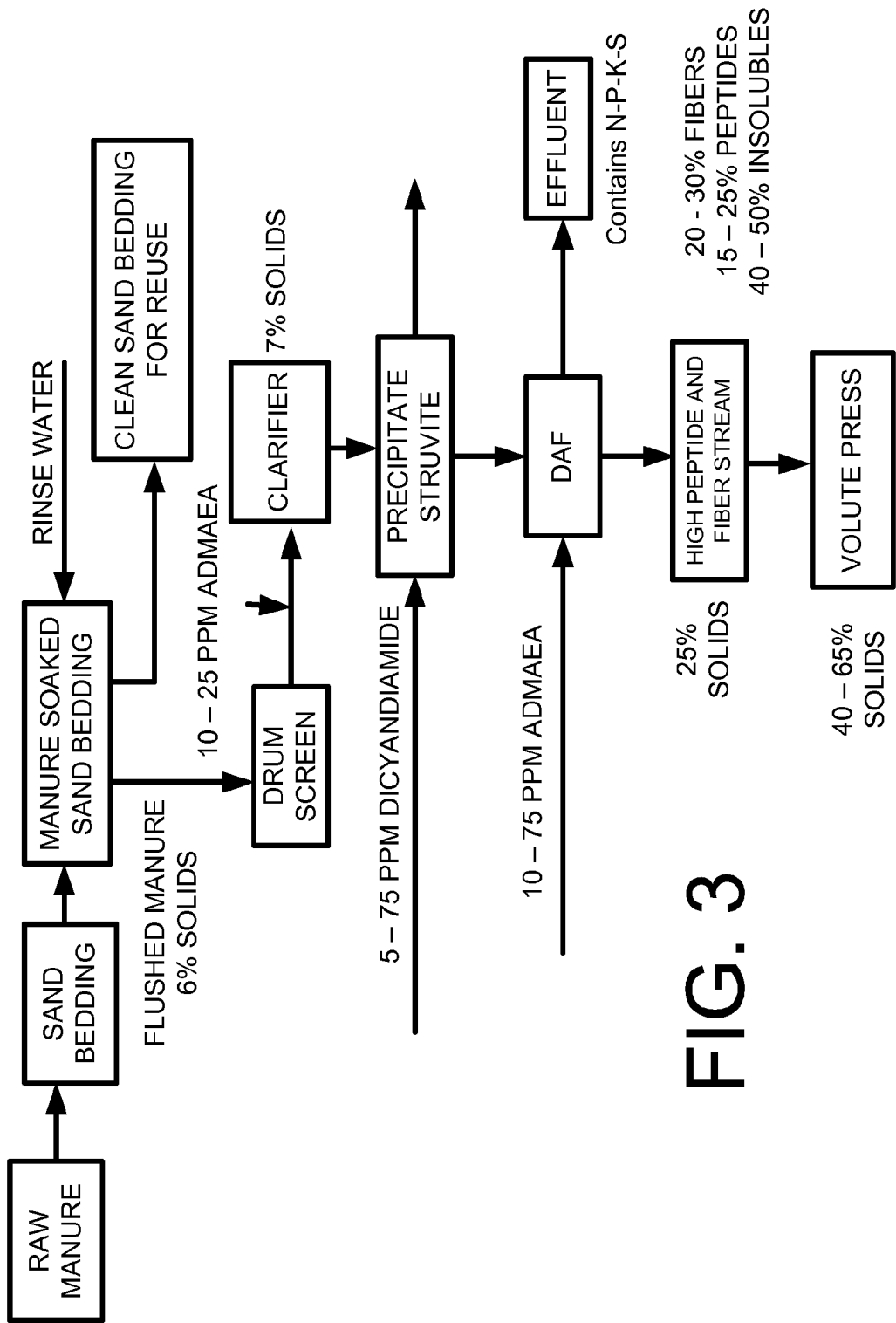
FIG. 3 is a flow chart of the process to recover amino acids, peptides and fibers from farm manure recovered from sand bedding.

In some farms, the cows deposit their waste onto sand beddings which over time become soaked and saturated with manure. The main benefit to using sand bedding in cow stalls to absorb the cow waste is decreased exposure to pathogens that can spread diseases to animals and humans. In an embodiment of the present invention, the manure is recovered from the sand bedding using rinse water that dilutes the manure prior to treatment. The treatment sequence is similar to that described in FIG. 1. The schematic of the process of treating manure recovered from sand bedding is illustrated in FIG. 3.

Information on the polymers used in the process of the present invention is provided below.

Polyamines

Molecular weight between 10,000 and 1,000,000

Liquid form with 40 to 50% concentration
Cationic site on the main chain
Viscosity at 50% concentration of between 40 and 20,000 centipoises
Any polyamine having two $H_2N$ groups may be used in this application. An example may be 1,3-diaminopropane.
Polydicyandiamide
Molecular weight: 3000 to 150,000
Cationic sites on a side chain
Liquid at 40 to 60% concentration
Highly cationic.
Viscosity of the liquids: 50 to 300 centipoises
Polydicyandiamide is obtained from the reaction of Dicyandiamide monomer and formaldehyde as shown below:

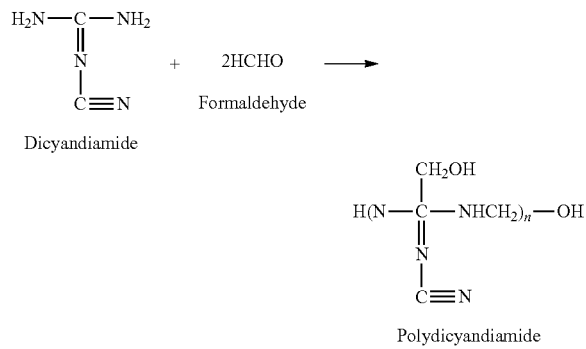

ADMAEA
Acrylamide-dimethylaminoethyl acrylate copolymers
The copolymerization of DMAEA-MeCl with acrylamide produces the cationic polymer
The main characteristics of the products obtained are:
Molecular weight: about 3 million to about 10 million
Viscosity at 5 g/l: 100 to 1700 cps.
Specifically: acrylamide/Ethanaminium, N,N,N-trimethyl-2-((1-oxo-2-propenyl)oxo)-, chloride copolymer is a useful form of ADMAEA in the present invention. The molecular formula is $C_{11}H_{21}ClN_2O_3$. The molecular structure is shown below in 2D.

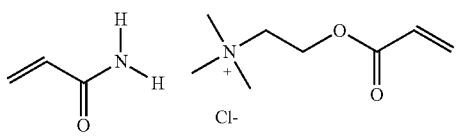

It should be understood, of course, that the foregoing relates to exemplary embodiments of the invention and that modifications may be made without departing from the spirit and scope of the invention.

RESULTS TABLE 1

D1: 50 ppm ADMAEA pre DAF liquid, centrifuge 5 min at 10000 rpm.
NO: Centrifuge 5 min at 10000 rpm without any polymer added.

| Sample Name | Total Coliforms MPN*/mL | E. coli MPN/mL |
| --- | --- | --- |
| Raw manure | $7.27 \times 10^5$ | $6.49 \times 10^5$ |
| Pre clarifier | $>2.42 \times 10^4$ | $>2.42 \times 10^4$ |
| After clarifier | $>2.42 \times 10^4$ | $>2.42 \times 10^4$ |
| Pre DAF | $7.27 \times 10^3$ | $4.88 \times 10^3$ |
| After DAF | $5.17 \times 10^3$ | $3.87 \times 10^3$ |

RESULTS TABLE 1-continued

D1: 50 ppm ADMAEA pre DAF liquid, centrifuge 5 min at 10000 rpm.
NO: Centrifuge 5 min at 10000 rpm without any polymer added.

| Sample Name | Total Coliforms MPN*/mL | E. coli MPN/mL |
| --- | --- | --- |
| DAF sludge | $>2.42 \times 10^4$ | $1.55 \times 10^4$ |
| D1 | 261 | 186 |
| No Polymer | 529 | 359 |

*:MPN is the most probable number in statistics which indicates how many bacteria cells in our case.

I claim:
1. A substantially continuous process for separating a stream rich in fibers, amino acids and peptides and a stream rich in minerals from raw farm manure, said process comprising the steps of:
providing a raw manure stream for treatment, said raw manure stream containing magnesium ammonium phosphate, calcium phosphate, amino acids, peptides, fibers and minerals, said minerals containing nitrogen, phosphorus, potassium and sulfur, said manure stream containing pathogen levels exceeding $6 \times 10^5$ MPN/mL;
mechanically removing particles having a predetermined size by a screening step;
reducing pathogen levels in the raw manure stream by between a factor of 3.3 to about a factor of 5, said reducing pathogen levels in the raw manure stream being accomplished by treating the raw manure stream in a clarifier at about 7 percent solids with between about 10 parts per million and about 25 parts per million on a dry weight basis of acrylamide/Ethanaminium, N,N,N-trimethyl-2-((1-oxo-2-propenyl)oxo)-, chloride copolymer, said acrylamide/Ethanaminium, N,N,N-trimethyl-2-((1-oxo-2-propenyl)oxo)-, chloride copolymer having a weight average molecular weight of between about 3 million and about 10 million;
precipitating magnesium ammonium phosphate and calcium phosphate, said precipitating being accomplished by the addition of between about 5 parts per million and about 75 parts per million on a dry weight basis of polydicyandiamide polymer, said polydicyandiamide polymer having a weight average molecular weight of between about 3000 and about 150,000; and
separating the stream rich in amino acids, peptides and fibers from the stream rich in minerals, said separating being accomplished in a dissolved air flotation device, said separating being accomplished by adding micronized air of a size between about 10 micrometers and about 20 micrometers at a rate between 5 to 10 cubic feet per hour to the dissolved air flotation device and by the addition of between about 10 parts per million and about 75 parts per million on a dry weight basis of acrylamide/Ethanaminium, N,N,N-trimethyl-2-((1-oxo-2-propenyl)oxo)-, chloride copolymer, said acrylamide/Ethanaminium, N,N,N-trimethyl-2-((1-oxo-2-propenyl)oxo)-, chloride copolymer having a weight average molecular weight of between about 3 million and about 10 million.
2. The process of claim 1, wherein the mineral rich stream contains at least 50 percent by weight of the nitrogen content in the raw manure stream, at least 75% of the phosphorus content by weight in the raw manure stream, at least 10 percent of the potassium content by weight in the raw manure stream, and at least 75% of the sulfur content by weight in the raw manure stream.

3. The process of claim 1, further comprising a volute press configured to remove water from the stream rich in amino acids, peptides and fibers to achieve a solids level of between about 40% to about 70%.

4. The process of claim 1, further comprising passing the raw manure stream through a sand bedding prior to mechanically removing the particles having a predetermined size by the screening step.

5. A substantially continuous process for producing a stream rich in amino acids and peptides from digested farm manure comprising the steps of:
   providing a digested manure stream for treatment, said manure stream containing amino acids, peptides, fibers and minerals, said minerals containing nitrogen, phosphorus, potassium and sulfur;
   precipitating magnesium ammonium phosphate and calcium phosphate, said precipitating being accomplished by the addition of a polydicyandiamide said polydicyandiamide polymer being added at between about 5 parts per million and about 75 parts per million on a dry weight basis of polydicyandiamide polymer, said polydicyandiamide polymer having a weight average molecular weight of between about 3000 and about 150,000;
   passing the digested manure stream through a rotating drum and a screw press for mechanically removing particles having a predetermined size; and
   separating a stream rich in amino acids, peptides and fibers, said separating being accomplished in a dissolved air flotation device by adding micronized air of a size between about 10 micrometers and about 20 micrometers at a rate between 5 to 10 cubic feet per hour to the dissolved air flotation device and by the addition of between about 10 parts per million and about 75 parts per million on a dry weight basis of acrylamide/Ethanaminium, N,N,N-trimethyl-2-((1-oxo-2-propenyl)oxo)-, chloride copolymer, said acrylamide/Ethanaminium, N,N,N-trimethyl-2-((1-oxo-2-propenyl)oxo)-, chloride copolymer having a weight average molecular weight of between about 3 million and about 10 million.

6. The process of claim 5, wherein the mineral rich stream contains at least 50 percent by weight of the nitrogen content in the raw manure stream, at least 75% of the phosphorus content by weight in the raw manure stream, at least 10 percent of the potassium content by weight in the raw manure stream, and at least 75% of the sulfur content by weight in the raw manure stream.

7. The process of claim 5, further comprising adding between about 5 parts per million and about 20 parts per million on a dry weight basis of a cationic polyamine having a weight average molecular weight of between about 10,000 and about 1 million, said cationic polyamine being added after the screw press.

8. The process of claim 5, further comprising a volute press configured to remove water from the stream rich in amino acids, peptides and fibers to achieve a solids level of between about 40% to about 70%.

* * * * *